United States Patent [19]
Boyd et al.

[11] Patent Number: 6,096,044
[45] Date of Patent: Aug. 1, 2000

[54] TEMPLATE ASSEMBLY FOR FACILITATING THE PLACEMENT OF INTERBODY FUSION DEVICES

[75] Inventors: Lawrence M. Boyd, Memphis; Eddie Ray, III, Cordova; Thomas McGahan, Memphis, all of Tenn.

[73] Assignee: SDGI Holdings, Inc., Wilmington, Del.

[21] Appl. No.: 09/111,203

[22] Filed: Jul. 7, 1998

Related U.S. Application Data

[60] Continuation-in-part of application No. 08/889,473, Jul. 8, 1997, Pat. No. 5,785,707, which is a division of application No. 08/427,432, Apr. 24, 1995, Pat. No. 5,645,549.

[51] Int. Cl.[7] .................................................. A61B 17/58
[52] U.S. Cl. ................................................................ 606/96
[58] Field of Search ................................ 606/37, 41, 45, 606/86, 61, 87, 96, 185, 116

[56] References Cited

U.S. PATENT DOCUMENTS

| | | |
|---|---|---|
| 3,848,601 | 11/1974 | Ma et al. . |
| 3,964,480 | 6/1976 | Froning . |
| 4,570,624 | 2/1986 | Wu . |
| 4,721,116 | 1/1988 | Schintgen et al. . |
| 4,772,287 | 9/1988 | Ray et al. . |
| 4,877,020 | 10/1989 | Vich . |
| 4,907,577 | 3/1990 | Wu . |
| 5,112,336 | 5/1992 | Krevolin et al. . |
| 5,133,720 | 7/1992 | Greenberg . |
| 5,195,505 | 3/1993 | Josefsen . |
| 5,389,104 | 2/1995 | Hahnen et al. .............................. 606/37 |
| 5,403,312 | 4/1995 | Yates et al. ................................. 606/41 |
| 5,489,292 | 2/1996 | Tovey et al. ................................ 606/37 |
| 5,531,744 | 7/1996 | Nardella et al. ............................ 606/41 |
| 5,645,549 | 7/1997 | Boyd et al. . |
| 5,665,092 | 9/1997 | Mangiardi et al. .......................... 606/86 |
| 5,807,393 | 9/1998 | Williamson, IV et al. ................. 606/41 |
| 5,810,863 | 9/1998 | Wolf et al. ................................. 606/185 |

FOREIGN PATENT DOCUMENTS

| | | |
|---|---|---|
| 516494 | 12/1992 | European Pat. Off. .................. 606/37 |
| 9207031 | 11/1992 | Germany . |
| 9217932 | 6/1993 | Germany . |
| 92 17 932 U | 7/1993 | Germany . |
| WO 94/17759 | 8/1994 | WIPO . |

Primary Examiner—Jeffrey A. Smith
Assistant Examiner—Eduardo C. Robert
Attorney, Agent, or Firm—Woodard, Emhardt, Naughton Moriarty & McNett

[57] ABSTRACT

A template assembly is provided for marking locations on the disc annulus for the implantation of an interbody fusion device or the introduction of a working instrument. The template assembly includes a tubular body sized for percutaneous introduction into a patient and advancement to an affected intervertebral disc. An elongated shaft slidably extends through the tubular body and is threadedly engaged to the handle-mounted thumb wheel so that rotation of the thumb wheel relative to the tubular body retracts the shaft through the body. A guide foot with a rotatable cam near the distal end of the tubular body is operable by the shaft and may be pivoted from a first position aligned with the tubular body to a second deployed position oriented transversely to the tubular body. The guide assembly has an electrocautery projection for marking locations on the disc annulus.

21 Claims, 11 Drawing Sheets

Fig. 20

TEMPLATE ASSEMBLY FOR FACILITATING THE PLACEMENT OF INTERBODY FUSION DEVICES

This application is a continuation-in-part of application Ser. No. 08/889,473 filed Jul. 8, 1997 now U.S. Pat. No. 5,785,707 which is a divisional application of Ser. No. 08/427,432 filed Apr. 24, 1995 now U.S. Pat. No. 5,645,549.

The present invention relates to a template to facilitate proper positioning of an implant into the intradiscal space between adjacent vertebrae. The template of this invention is particularly useful in connection with interbody fusion devices, especially of the type shown and described in pending application Ser. No. 08/411,017, filed on Mar. 27, 1995, owned by the assignee of the present invention and naming common inventors.

One of the most common sources of low back pain is damage or defects in the spinal disc separating adjacent vertebrae. The disc can be herniated or suffering from a variety of degenerative conditions, so that in either case the anatomical function of the spinal disc is disrupted. In recent years the most prevalent treatment for these types of conditions has been to fuse the two adjacent vertebrae together, thereby eliminating the normal movement of the affected disc. Depending upon the condition of the disc, the entire disc may be removed, or the disc annulus can be left intact with some or all of the disc nucleus removed.

Figure 1:
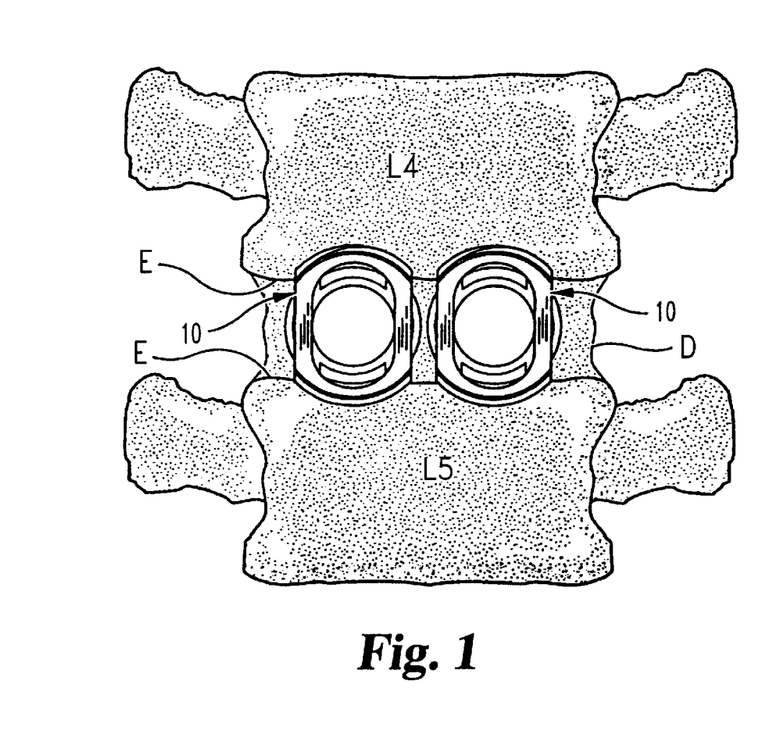
FIG. 1 is an elevational view of the anterior aspect of the L4–L5 motion segment shown instrumented with a pair of interbody fusion devices.
Figure 2:
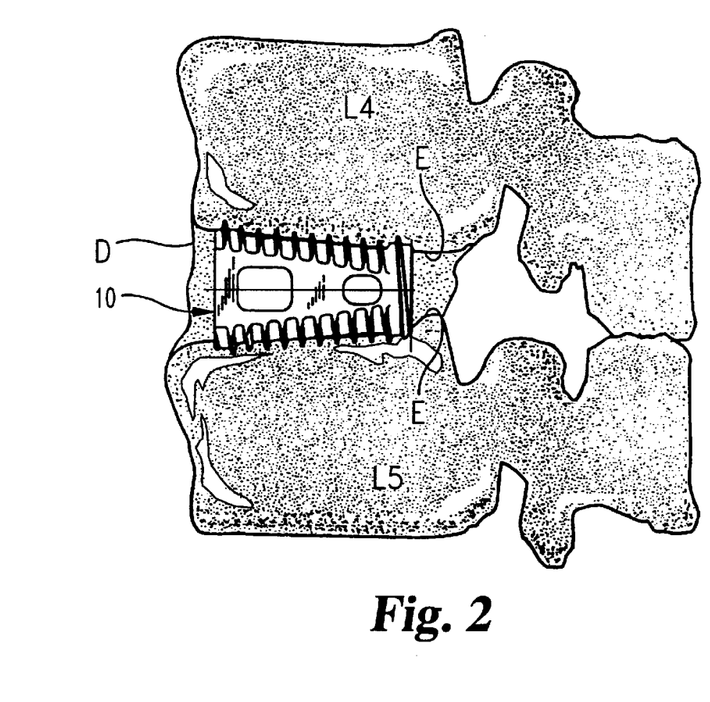
FIG. 2 is a side elevational view of the motion segment and fusion device construct depicted in FIG. 1.

With the removal of the disc or disc nucleus, something is required in the intradiscal space to maintain the normal anatomic position of the adjacent vertebrae, at least until fusion occurs. One common device for maintaining the disc space is the interbody fusion device. In one type of interbody fusion device, multiple such implants are disposed between the adjacent vertebrae, separated by space to receive bone graft material. An example of one such device is found in the above-mentioned co-pending application, Ser. No. 08/411,017, entitled INTERBODY FUSION DEVICE AND METHOD FOR RESTORATION OF NORMAL SPINAL ANATOMY, filed on Mar. 27, 1995, which disclosure and figures are incorporated by reference. Bilateral placement of two such fusion devices is depicted in FIGS. 1 and 2. The device 10 is tapered to maintain the normal curvature of the vertebral level (L4–L5), and is threaded for engagement with the vertebral end plates E. The device 10 can be implanted through portals formed in the disc annulus D. As illustrated in FIGS. 1 and 2, two fusion devices 10 are implanted to fill the disc space, effectively maintain the spinal curvature and provide adequate space between the implants to be filled with bone graft material.

In the operative procedure for implanting the fusion device, a midline incision is made to expose the anterior aspect of the vertebral bodies at least one level above and below the affected motion segment. The soft tissues are denuded at the target disc to provide adequate space to implant the fusion device. Placement and positioning of the fusion device is typically assessed under direct vision, and the depth of insertion of the device assessed through lateral x-ray.

One difficulty with current techniques for implanting multiple implants arises in determining the proper position for the implants to avoid interference between the implants within the disc space and to maintain adequate spacing between the implants to receive bone graft material. There is a need for a simple device, or template, that can be easily used by the spinal surgeon to determine the optimum position for implanting a fusion device. In U.S. Pat. No. 4,772,287 to Dr. Charles Ray et al., a posterior technique is described in which holes are drilled through each of the facet joints to provide a window for insertion of prosthetic disc capsules. Although in this technique the windows act as a guide for the insertion instruments, the size and orientation of these guide windows is severely limited by the facet joint itself. For example, in the '287 patent, the holes through the facet joints are 11-mm, which is an appropriate size for the smaller implant described in that patent. However, larger implants, such as that described in the above-mentioned co-pending application, cannot fit through the same small hole, and instead require complete removal of the facet joint. Moreover, since the technique described in the '287 relies upon the facet joint as a guide, it cannot be implemented in an anterior approach. Thus, the surgical approach described in this Ray patent cannot be used to implant the anterior fusion devices disclosed in the above-mentioned co-pending application Ser. No. 08/411,017.

Another approach as described in U.S. Pat. No. 3,964,480, to Froning, is to use a stereotactic fixture to align instruments puncturing the disc annulus. The '480 patent describes the use of this fixture to provide unobstructed puncture of the intervertebral disc for injection of fluids, such as radiographic contrast fluids and decompression drugs, such as chymopapain. However, as is evident from the figures of the '480 patent, the described stereotactic fixture is large and unwieldy, and certainly does not lend itself well as a simple device for determining the position for implantation of a fusion device. In addition, the stereotactic fixture in the '480 patent is not suited for approaching the disc space anteriorly.

The need of spinal surgeons for a device for positioning of multiple implants within the intervertebral space is not adequately met by any of these prior devices or techniques. This need is magnified when such implants are placed via trocars and video-assisted spinal surgery methods, where exposure of the disc space is more difficult and accurate surgical orientation more critical. What is needed is a simple and easily used template that allows a surgeon to readily locate where an implant should be inserted into the intradiscal space.

SUMMARY OF THE INVENTION

This unresolved need is met by the template assembly of the present invention. In one embodiment, the template assembly comprises a tubular body sized for percutaneous introduction into the human body, and particularly for introduction to the disc annulus. The tubular body has a proximal end residing outside the patient and a distal end residing adjacent the disc annulus when the template is in use. The template assembly further comprises an elongated guide foot pivotably connected to the distal end of the tubular body by a hinge. The guide foot initially assumes a first retracted position in which the foot is aligned with the longitudinal axis of the tubular body to facilitate introduction of the template via a seal or working channel anchored to the skin. The guide foot is pivotable to a second deployed position in which the foot is oriented at an angle relative to the longitudinal axis of the tubular body. In this position, the guide foot can rest against the disc annulus.

The template assembly includes an elongated deployment shaft sized to slidably extend through the tubular body to project beyond the distal end of the body. The deployment shaft has a generally rounded or blunt distal tip to bear against the guide foot as the shaft is pushed through the tubular body. In particular, as the shaft is advanced through the body, the rounded tip pushes against the guide foot to cause the foot to pivot about the hinge from the guide foot's first position to its second deployed position. To insure a controlled deployment of the guide foot, the elongated shaft is threadedly engaged to the tubular body so that rotation of the shaft relative to the tubular body achieves controlled advancement of the shaft through the body. A handle at the proximal end of the deployment shaft provides adequate purchase for the surgeon to rotate the shaft.

In one embodiment of the inventive template assembly, the guide foot includes a guide bore extending therethrough. The guide bore is sized to receive the operative end of a marking instrument, such as the working tip of an electrocautery device. In use, the template assembly is initially introduced, preferably percutaneously, into the spinal space at the affected vertebral level. During initial introduction, the deployment shaft is retracted into the tubular body and the guide foot is oriented in its first position aligned with the longitudinal axis of the body, thereby presenting the smallest profile possible. When the distal end of the tubular body is near the disc annulus, the deployment shaft is advanced through the tubular body to gradually push the guide foot to its pivoted second position.

With the guide foot in its deployed position, the elongated shaft can be removed from the tubular body to permit introduction of a guide wire through the body. The guide wire is used to puncture the disc annulus and provide an anchor and a pivot point for the template assembly. With the guide wire firmly engaged in the spinal disc the guide foot is moved into contact with the disc annulus. An electrocautery instrument is then introduced with its tip extending through the guide bore in the foot. The energized tip cauterizes the disc annulus, thereby marking the proper position for insertion of an interbody fusion device. The template assembly is then pivoted about the anchored guide wire so that the guide foot is positioned at the opposite side of the disc annulus. A second mark is made with the electrocautery instrument through the guide bore to denote the position for insertion of a second fusion device. The guide wire and template assembly can then be removed. As the template assembly is removed, the tissue surrounding the surgical site will push against the guide foot causing it to pivot back to its first position aligned with the tubular body.

In a second embodiment, the guide foot does not include a guide bore, but instead includes a feature for itself marking the disc annulus. The guide foot can include a projection from the surface facing the disc that serves as an electrocautery tip. The template assembly includes an electrical connection for providing electrical energy to the projection of the guide foot.

In another embodiment the template assembly facilitates the placement of an implant or instrument at a portion of the spine, such as the disc space between adjacent vertebrae. The template assembly comprises a tubular body sized for introduction into a patient for advancement to a portion of the spine. The tubular body has a longitudinal axis, a proximal end disposed outside the patient, a spike extending from the distal end of the tubular body along its longitudinal axis and an elongated guide foot. The guide foot has a first end and second end and is connected to a rotatable cam in the tubular body at the first end whereby the guide foot is pivotable outward from a first position in which the second end is adjacent the spike for introduction into the patent. A variable second position of the second end is at a known distance from the spike and a deployment means extends through the tubular body and operates the guide foot causing the guide foot to pivot between the first position and the variable second position.

In another embodiment, a template assembly facilitates the placement of an implant or instrument at a portion of the spine, such as the disc space between adjacent vertebrae. The template assembly comprises a tubular body sized for introduction into a patient for advancement to a portion of the spine. The tubular body has a longitudinal axis, a proximal end disposed outside the patient, and a distal end disposed adjacent the portion of the spine when the tubular body is within the patient; a spike extending from its distal end along the longitudinal axis of the tubular body, and an elongated guide foot. The guide foot has a first end and second end and connects to a rotatable cam in the tubular body at the first end whereby the guide foot is pivotable between a first position in which the second end is adjacent the spike for introduction into the patient, and a variable second position in which the second end is at a known distance from the spike; and deployment means extending through the tubular body and operating on the guide foot causing the guide foot to pivot between the first position and the variable second position. The deployment means includes a drive rod and a driver within the tubular body and the drive rod is threadedly engaged to a knob disposed outside the tubular body, whereby the drive rod advances through the tubular body by rotation of the knob.

One object of the present invention is to provide a template to facilitate accurate positioning of implants within the intradiscal space. A further object resides in features of the invention that permit percutaneous introduction and use of the template assembly. Yet another object is to provide a template assembly that can be easily used to mark the disc annulus, and that can be easily and quickly removed afterwards.

One important benefit of the template assembly of the present invention is that it provides the surgeon with an accurate mark for positioning multiple implants within the intradiscal space. Another benefit is that the template assembly can be readily adapted to accommodate different sizes of implants and readily oriented to mark different locations around the disc annulus.

Other objects and benefits of the inventive template assembly will become apparent upon consideration of the following description of the invention and the accompanying figures.

DESCRIPTION OF THE PREFERRED EMBODIMENTS

For the purpose of promoting an understanding of the principles of the present invention, reference will be made to the embodiments illustrated in the accompanying drawings and specific language will be used to describe the same. It is understood that the specific language and figures are not intended to limit the scope of the invention only to the illustrated embodiment. It is also understood that alterations or modifications to the invention or further application of the principles of the invention are contemplated as would occur to persons of ordinary skill in the art to which the invention relates.

Figures 3, 4, 5:
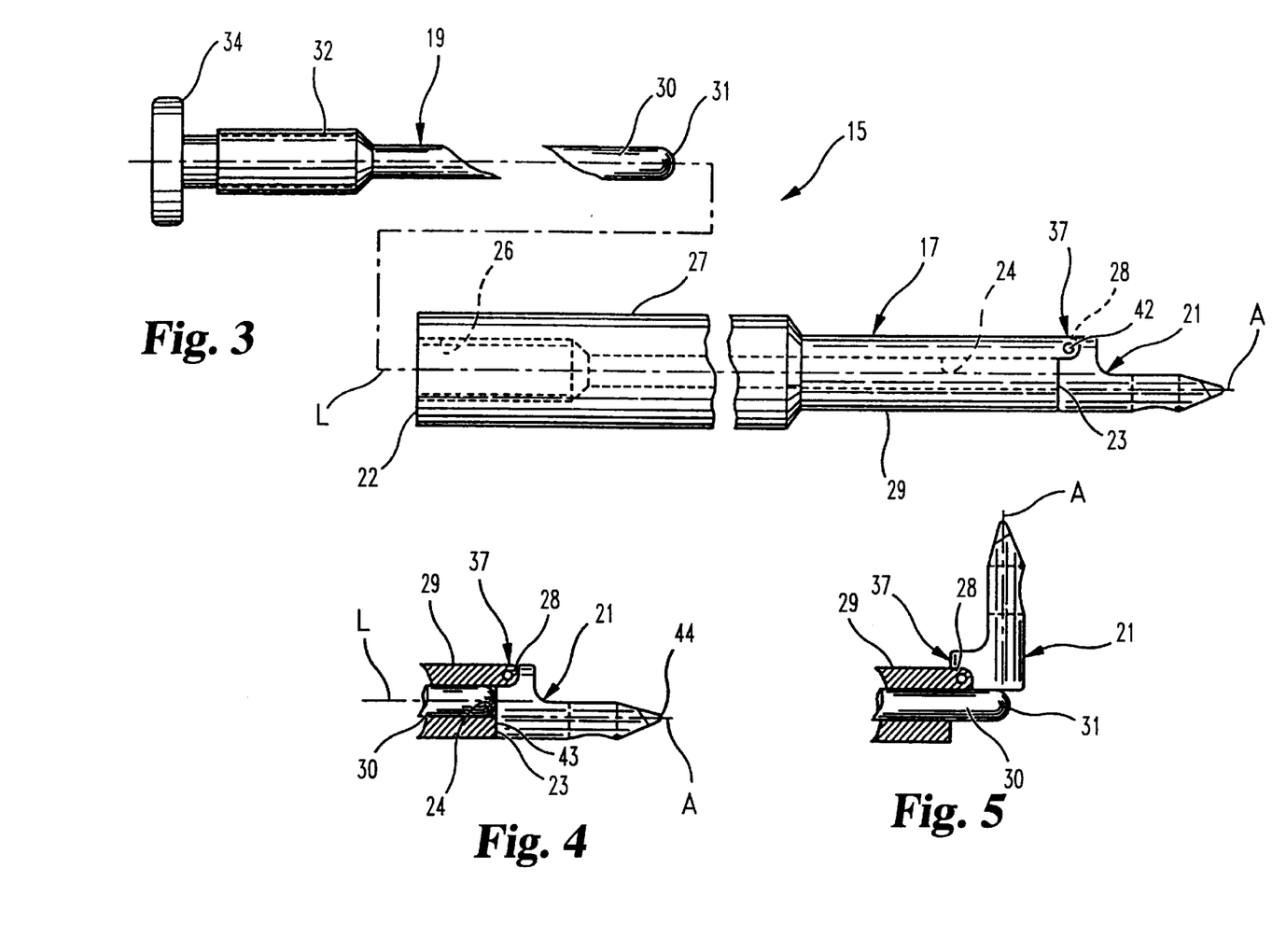
FIG. 3 is an exploded view of the components of the template assembly according to one embodiment of the present invention.
FIG. 4 is an enlarged partial cross-sectional view of the distal tip of the template assembly illustrated in FIG. 3, shown with the guide foot in its initial insertion position.
FIG. 5 is an enlarged partial cross-sectional view of the distal tip as illustrated in FIG. 4, shown with the guide foot in its second deployed position.

Referring now to FIG. 3, a template assembly 15 in accordance with the preferred embodiment of the invention is illustrated. The template assembly 15 includes an outer tubular body 17, an inner deployment shaft 19 and a guide foot 21. The tubular body 17 is elongated along a longitudinal axis L between its proximal end 22 and its distal end 23. In use, the proximal end 22 is disposed outside the skin of the patient while the distal end 23 is situated adjacent the disc annulus of the affected motion segment.

The tubular body 17 defines a central bore 24 from end to end to slidably receive the deployment shaft 19. At the proximal portion 27 of the tubular body 17, the central bore 24 includes a threaded bore 26. The proximal portion 27 is larger than the distal portion 29 of the tubular body 17, primarily to provide a smaller profile in the region of the vertebrae. In addition, the larger diameter of the proximal portion 27 provides a better grip for the spinal surgeon manipulating the template assembly 15 in situ. The deployment shaft 19 includes an elongated probe 30 configured to project beyond the distal end 23 of the tubular body 17 and having a generally rounded or blunt tip 31 for reasons set forth below. At the proximal end of the deployment shaft 19 is a threaded portion 32 having threads that mate with the threaded bore 26 of the tubular body 17. The proximal end of the deployment shaft is configured into a handle or knob 34 adapted to facilitate rotation of the deployment shaft 19 within the tubular body 17. The knob 34 is preferably circular with knurling or other gripping feature defined on the circumference of the knob facilitate manual rotation of the knob.

Figure 6:
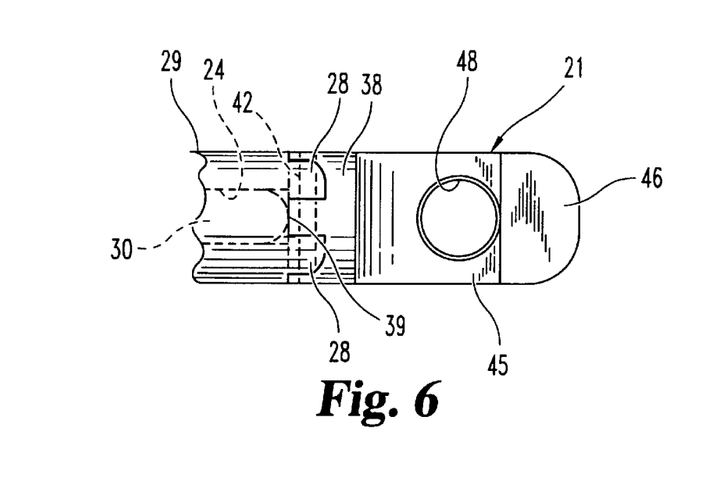
FIG. 6 is a partial top elevational view of the distal tip of the template assembly as illustrated in FIG. 4.
Figure 7:
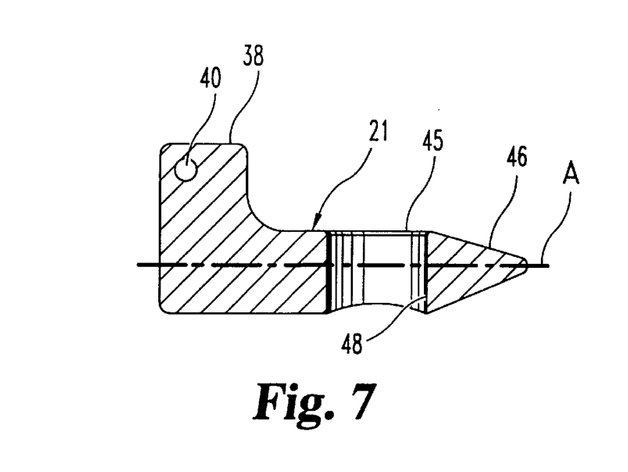
FIG. 7 is a side cross-sectional view of the guide foot.

Details of the guide foot 21 and its connection to the tubular body 17 can be discerned from FIGS. 7–10. In particular, the guide foot 21 includes a hinge portion 38 and a guide portion 45, with the portions preferably oriented at right angles so that the guide foot takes on the shape of an "L", as seen in FIG. 7. The hinge portion 38 of the guide foot defines a hinge boss 39 that is disposed between a pair of hinge flanges 28 projecting from the distal end 23 of the tubular body 17, as best seen in FIGS. 4 and 6. A hinge pin 42 passes through bores in the hinge flanges 28 and a hinge bore 40 defined in the hinge boss 39 of the guide foot.

Figure 8:
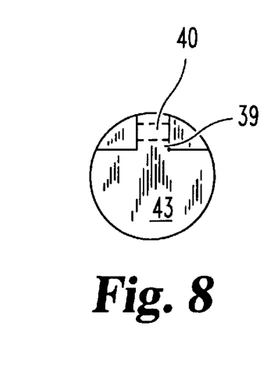
FIG. 8 is an end elevational view of the proximal end of the guide foot.
Figure 9:
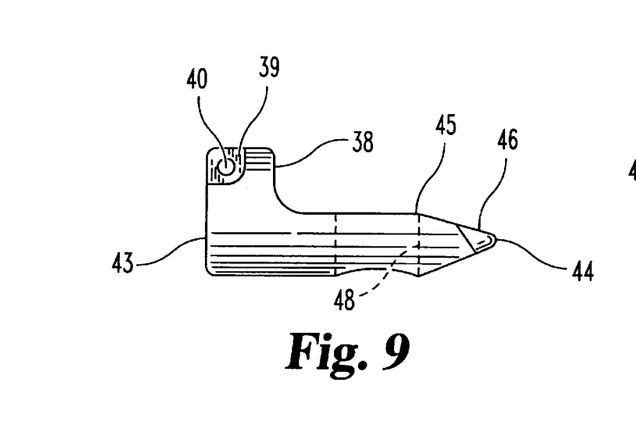
FIG. 9 is a side elevational view of the guide foot.
Figure 10:
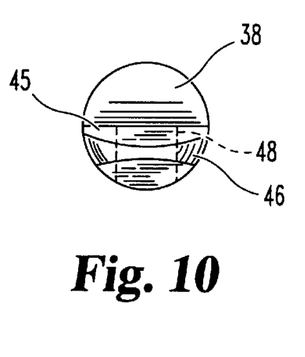
FIG. 10 is an end elevational view of the distal end of the guide foot.

The hinge portion 38 of the guide foot 21 defines a proximal face 43 that is closely adjacent the distal end 23 of the tubular body when the guide foot is in its first retraced position shown in FIGS. 3–4. In this first position the axis A of the guide portion 45 of the guide foot is aligned with the longitudinal axis L of the tubular body. The guide foot 21, and particularly the hinge portion 38, is circular in profile, as depicted in FIG. 8, with an effective outer diameter substantially equal to or less than the outer diameter of the tubular body 17. Thus, the guide foot 21 presents a profile that is no larger than the tubular body, which is a beneficial feature for percutaneous introduction of the template assembly 15. The guide portion 45 of the guide foot also includes a tapered tip 46 at its distal end 44 to reduce the risk of trauma to the tissue at the surgical site during introduction of the template assembly.

As can be seen in FIGS. 3–5 the guide foot 21 is pivotably connected to the tubular body 17 at the hinge 37. The hinge 37 is offset to one side of the tubular body to take advantage of the "L" shape of the guide foot 21. The guide foot 21 initially assumes its first position, shown in FIGS. 3–4, in which the axis A of the guide portion 45 of the guide foot is aligned with, and preferably parallel to, the longitudinal axis L of the tubular body 17. The guide foot 21 is pivotable to its second deployed position in which the axis A of the foot is at an angle, preferably perpendicular, to the longitudinal axis L, as shown in FIG. 5. The guide foot 21 is pushed from the first position of FIG. 4 to the second position of FIG. 5 by the rounded tip 31 of the elongated probe 30.

The guide portion 45 of the guide foot 21 includes a guide bore 48 defined therethrough. The guide bore 48 is sized to receive the working tip of a marking instrument. Preferably, the marking instrument is an electrocautery instrument that cauterizes the disc annulus. The marking instrument must be capable of leaving a mark on the annulus sufficient to be visually observed by the spinal surgeon. This mark will identify the proper position for inserting an implant into the disc space. Typically, the annulus will be fenestrated at the mark in order to receive an interbody fusion device, such as the device described above.

Steps in the use of the template assembly 15 are depicted in FIGS. 11a–13b. In the first step, the patient's skin S is punctured to receive a sealed trocar 50. The trocar 50 optimally provides a working channel for the template assembly 15, as well as for diskectomy instrumentation, fusion devices and insertion instrumentation to be used subsequently. One significant advantage achieved by the template assembly 15 according to this invention is that it is well suited for use in percutaneous endoscopic procedures. It has been found that diskectomies and even fusions can be performed using minimally invasive techniques, without the necessity of the more difficult and invasive surgical procedures of the past.

Figures 11A, 11B, 12A, 12B, 13A, 13B:
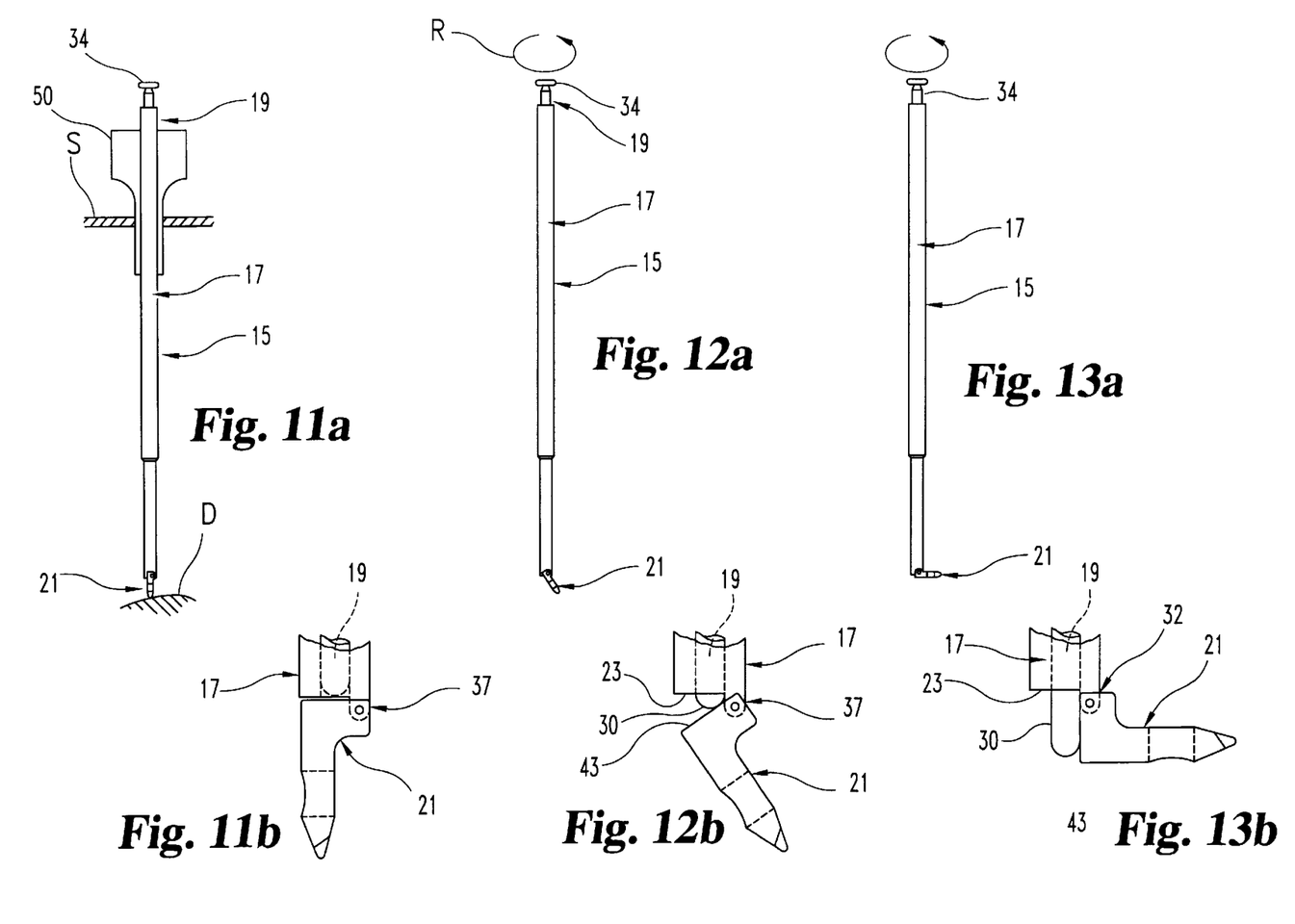
FIGS. 11a–11b are pictorial representations of the template assembly percutaneously inserted into the patient.
FIGS. 12a–12b are pictorial representations of the template assembly as the guide foot is being deployed.
FIGS. 13a–13b are pictorial representations of the template assembly with the guide foot fully deployed.

With the sealed trocar 50 anchored to the skin S, the template assembly 15 is introduced with the guide foot 21 in its first position, as depicted in FIG. 11b. The deployment shaft 19 is retracted within the tubular body 17 during this step so that the rounded tip 31 does not project beyond the distal end 23 of the body. Once the guide foot 21 contacts the disc annulus D the template assembly 15 is withdrawn slightly to allow the guide foot to be pushed and pivoted to its second position. The deployment shaft 19 is advanced through the tubular body 17 by rotating the knob 34 in the direction R shown in FIG. 12a. As the knob 34 and deployment shaft 19 is rotated, the probe 30 bears against the proximal face 43 of the guide foot 21 to cause the foot to pivot about the hinge 37. As the probe 30 moves farther beyond the distal end 23 of the tubular body 17, the guide foot pivots progressively through the position shown in FIG. 12b to its second fully deployed position shown in FIG. 13b.

Figure 14:
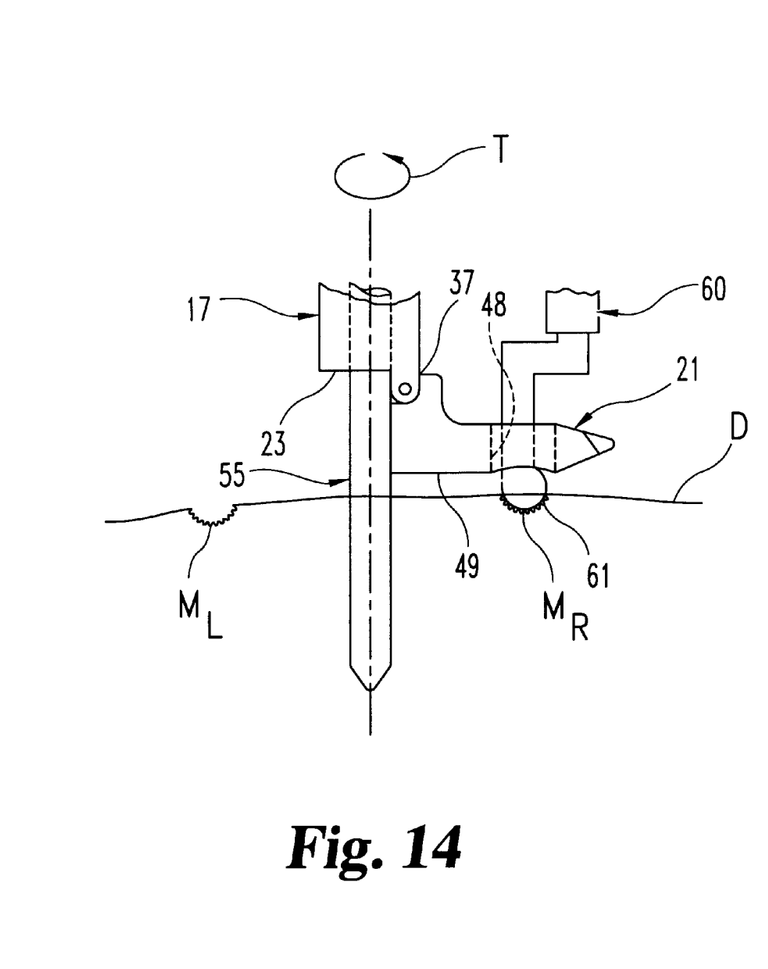
FIG. 14 is an enlarged pictorial representation of the template assembly anchored to the disc and showing the use of an electrocautery instrument in connection with the deployed guide foot for marking the disc annulus.

With the guide foot 21 in its second position, the template assembly 15 is advanced toward the disc until the bottom surface 49 of the foot is against the disc annulus D. The deployment shaft 19 can be removed and replaced with a guide wire 55, as shown in FIG. 14. The guide wire has a sharp tip to pierce the disc annulus D and may include means to limit and control advancement of the guide wire into the disc. The guide wire is advanced into the disc a sufficient distance to effectively anchor the template assembly 15 in position with the guide foot 21 in contact with the annulus D. An electrocautery instrument 60 is then introduced to the surgical site so that the working tip 61 extends through the guide bore 48 in the guide foot 21. The working tip 61 is energized to cauterize the disc annulus D leaving a mark $M_R$ on the annulus. This mark $M_R$ is visible to the surgeon to identify the proper location for insertion of an implant into the disc space. With the guide wire 55 still anchored in the disc, the entire template assembly 15 can be pivoted about the guide wire in the direction T shown in FIG. 14. The guide foot 21 is then oriented on the left side of the guide wire, on the opposite side of the disc from the first mark $M_R$. A second mark $M_L$ can then be made on the disc annulus D using the electrocautery instrument. Once all the necessary marks are made on the disc annulus, the guide wire can be withdrawn, followed by the template assembly 15. As the assembly is withdrawn from the surgical site, the surrounding tissue bears against the guide foot 21 to cause it to pivot about the hinge 37 and return to its first low-profile position.

Figure 15:
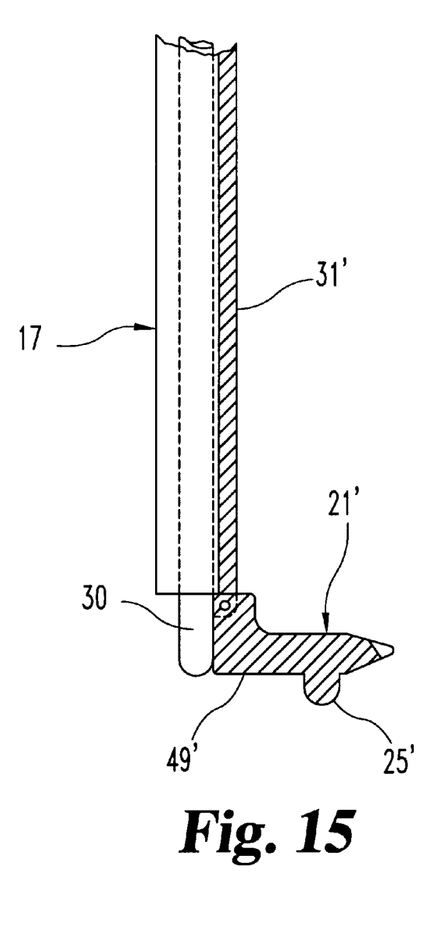
FIG. 15 is a side elevational view of another embodiment of the template assembly in which the guide foot carries an electrocautery projection for marking the disc annulus.

In an alternative embodiment, shown in FIG. 15, the guide foot 21' is modified from the foot 21 shown in FIG. 14. Specifically, the guide bore 48 is eliminated in favor of an electrocautery projection 25' formed in the bottom surface 49' of the guide foot. An electrical attachment 31' provides electrical energy to the guide foot 21'. In this instance, the guide foot 21' is formed of an electrically conductive material and the projection 25' is configured to emulate the working tip of an electrocautery instrument. One benefit of this configuration is that it is not necessary to introduce a separate electrocautery instrument to the surgical site.

The components of the template assembly 15 are sized for percutaneous introduction to the disc. In one specific embodiment, the assembly has an overall length of 12.5 in. (31.75 cm) from the proximal end 22 of the tubular body 17 to the distal end 44 of the guide foot 21 in its retracted first position. The tubular body 17 has an outer diameter in the specific embodiment of about 0.437 in. (1.11 cm) at the proximal portion 27 and of about 0.250 in. (0.63 cm) at the distal portion 29. The central bore 24 of the tubular body 17 has a diameter of 0.125 in. (0.32 cm), while the deployment shaft has a diameter of 0.120 in. (0.30 cm) to be slidably disposed within the central bore. The mating threads between the deployment shaft 19 and the tubular body 17 are preferably ¼-20 UNC-2B threads.

In one specific embodiment, the guide foot 21 has an effective outer diameter of 0.250 in. (0.63 cm) and a length from proximal face 43 to the distal end 44 of 0.541 in. (1.37 cm). The guide bore 48 has a diameter of 0.136 in. (0.35 cm) with its center being located 0.313 in. (0.80 cm) from the proximal face 43. The distance to the center of the guide bore 48 establishes the spacing between the two marks $M_R$ and $M_L$ made on the disc annulus D to identify the location for insertion of the fusion implants. Referring again to FIG. 14, it can be seen that the mark $M_R$ is made at predetermined distance from the guide wire 55 anchored in the disc. When the template assembly is pivoted about the guide wire, the mark $M_L$ is separated from the mark $M_R$ by twice that predetermined distance. This distance between marks is determined by the necessary separation between the interbody fusion devices to be introduced into the intradiscal space. In the specific illustrated embodiment, the fusion devices may have a maximum diameter of about 0.787 in. (2.00 cm), which requires the two marks $M_R$ and $M_L$ to be at least that distance apart.

In the illustrated embodiments, the template assembly is configured to mark the location for insertion of two bilateral fusion devices in the lower lumbar spine. Naturally, the dimensions of the guide foot 21 and the guide bore 48, or cauterizing projection 25' will be reduced in accordance with the geometry of the spinal anatomy at the affected motion segment. In addition, the template assembly can be configured to provide guide marks for the implantation of more than two fusion devices. In procedures involving three or more such devices, the template assembly can be oriented over successively made marks with the guide wire anchored into the disc at the marks. New marks can be made in the described fashion by pivoting the template assembly about the guide wire. The distance to the center of the guide bore 48 or cauterization projection 25' would be reduced accordingly.

Figure 16:
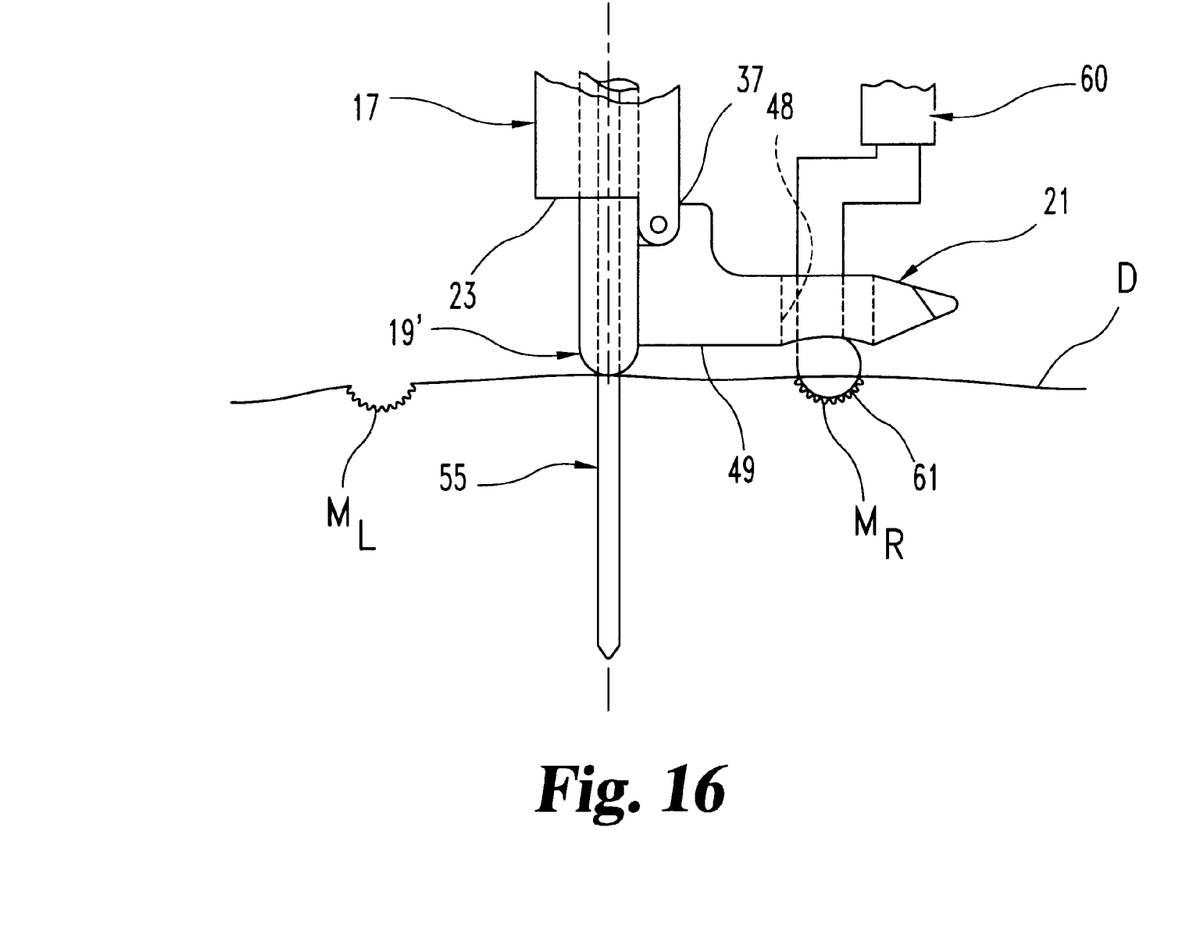
FIG. 16 is an enlarged pictorial representation of a template assembly anchored to the disc showing an alternative embodiment of the deployment shaft and guide wire.

Two embodiments of the invention have been illustrated and described in detail in the foregoing description and accompanying drawings. Other embodiments are shown in FIG. 16 and following. For example, the template assembly 15 has been described as used with a separate guide wire 55 to anchor and orient the assembly during the marking steps.

In the embodiments described in detail above, the deployment shaft 19 was required to be removed to accommodate the guide wire 55. Alternatively, the deployment shaft can be cannulated to receive the guide wire therethrough. In this embodiment, shown in FIG. 16, the deployment shaft 19' need not be removed. The rounded tip 31 of the deployment shaft will not traumatize the disc annulus. The diameter of the deployment shaft is sufficient to accept a thin guide wire.

The guide foot 21 has been described and depicted as having an "L" shape. Other configurations are contemplated by this invention, provided that the guide bore or cauterization projection can be maintained at the predetermined distances discussed above. In accordance with the present invention, the components are contemplated to be formed from surgical grade stainless steel or other medically suitable material. The guide foot can be composed of a plastic material to minimize heat conduction from the working tip of the electrocauterization instrument. Alternatively, the device may be fabricated of a radioluscent plastic or composite material to allow unimpeded viewing of the guide wire placement and anatomical orientation. Other suitable materials for the components of the template assembly 15 are contemplated.

Referring to FIGS. 17a through 17g, an alternative embodiment not using the "L" shaped foot is shown. Template assembly 100 has outer tubular body 101 extending along a longitudinal axis B between its proximal end 103 and its distal end 104. A yoke assembly 120 is fixed to the distal end 104 of the body 101. A round spike 110 with a tip 116 is fixed to the distal end 135 of the yoke assembly and extends along the longitudinal axis B of the tubular body 101. Spike 110 may be integrally formed with distal end 135 of the yoke assembly. In a preferred embodiment spike 110 has external threading 136 which mates with internal threading 136' formed in the distal end 135 of the yoke assembly. Guide foot 111 has a tip 117, preferably tapered, extends generally in the longitudinal direction away from distal end 104 of the tubular body 101. The guide foot 111 is connected to a cam 113 which sits on a pivot pin 112. Guide foot 111 may be integrally formed with cam 113 or it may be affixed by a bolt, screw, adhesive or other means known in the art. The cam 113 can turn on the axis of the pivot pin 112 upon which it sits.

Figure 17A:
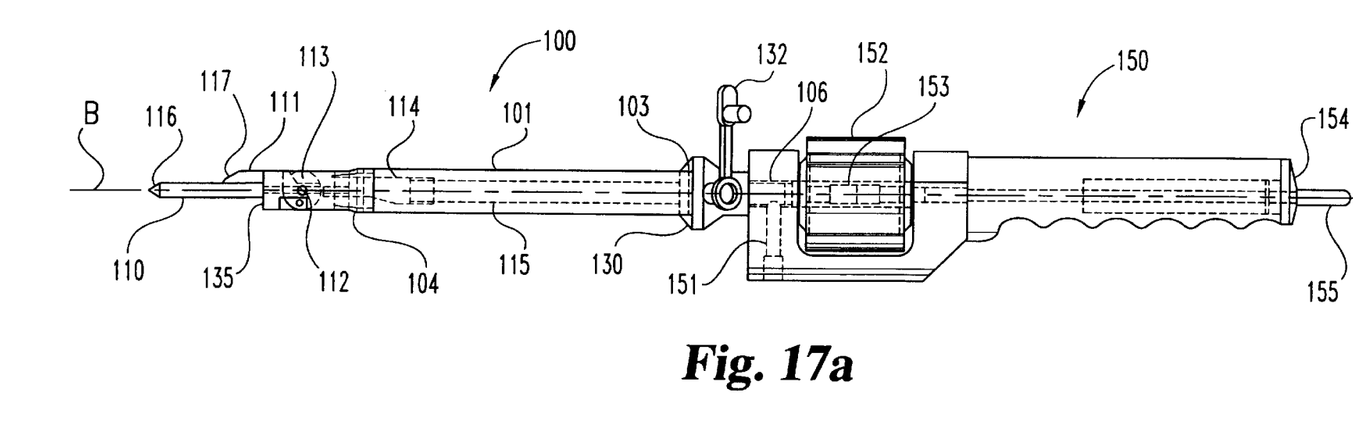
FIGS. 17a–17b are partial views of the side and top of another embodiment of the template assembly.
Figure 17B:
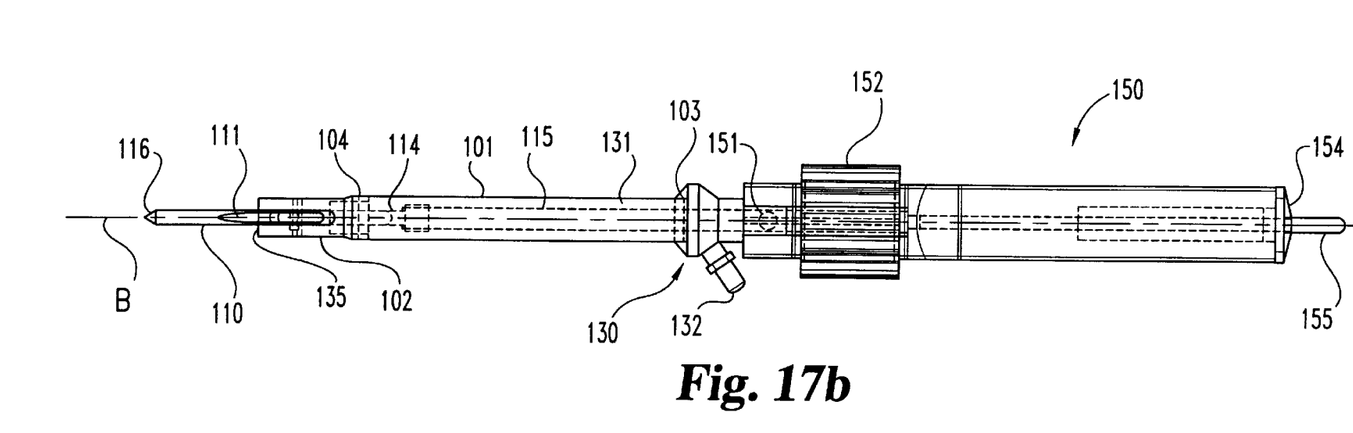
Figure 17C:
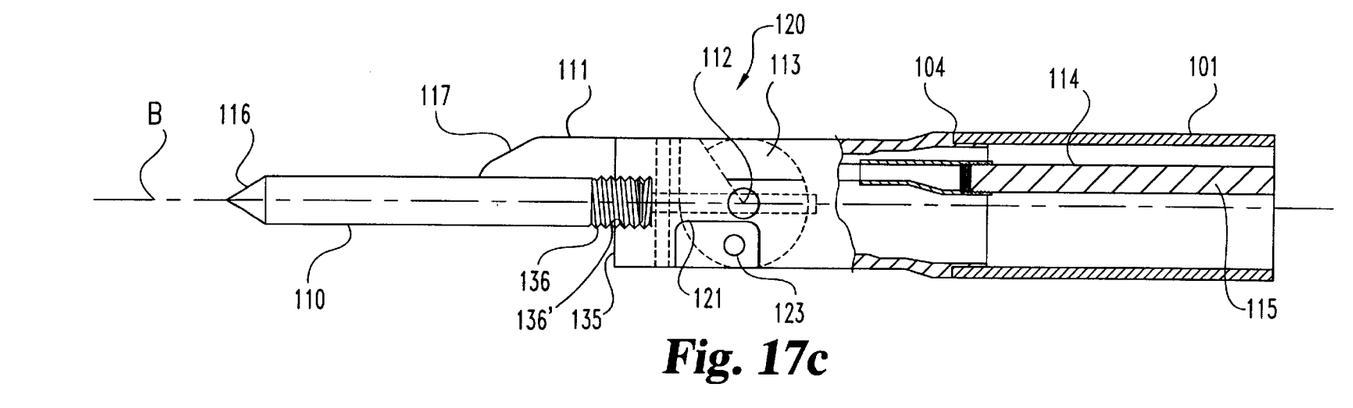
FIGS. 17c and 17d are enlarged partial fragmented cross sectional views of the distal tip of the template assembly illustrated in FIGS. 17a and 17b shown with the guide foot in its initial insertion position and second deployed position respectively.
Figure 17D:
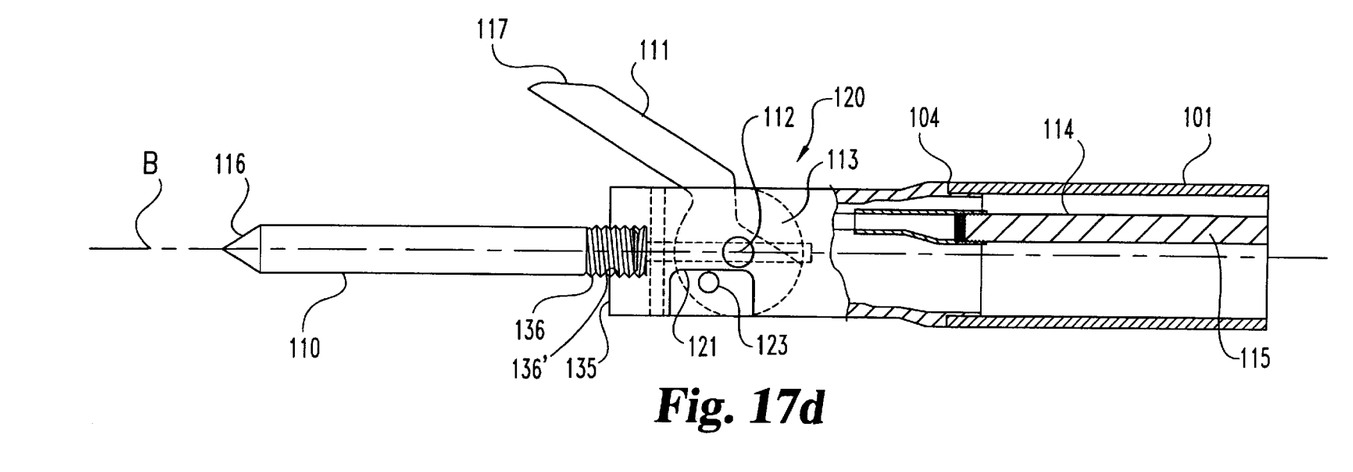
Figure 17E:
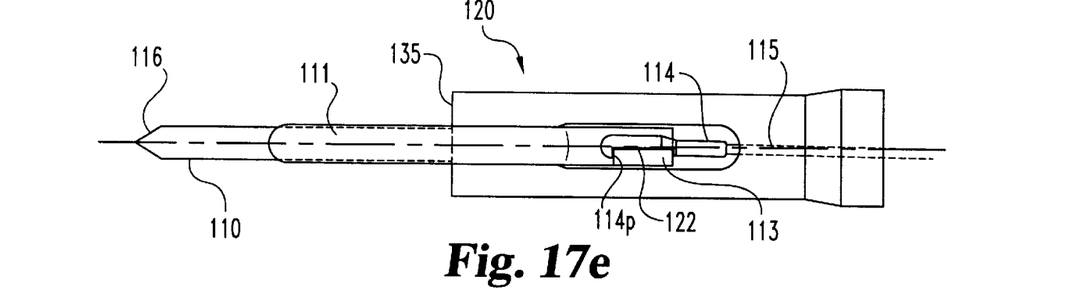
FIGS. 17e–17g are enlarged partial cross sectional views of the distal tip of the template assembly illustrated in FIGS. 17a–17d with slightly different guide foot operating details, showing top and side views of the guide foot in its initial insertion position and a side view of the guide foot in its second deployed position.
Figure 17F:
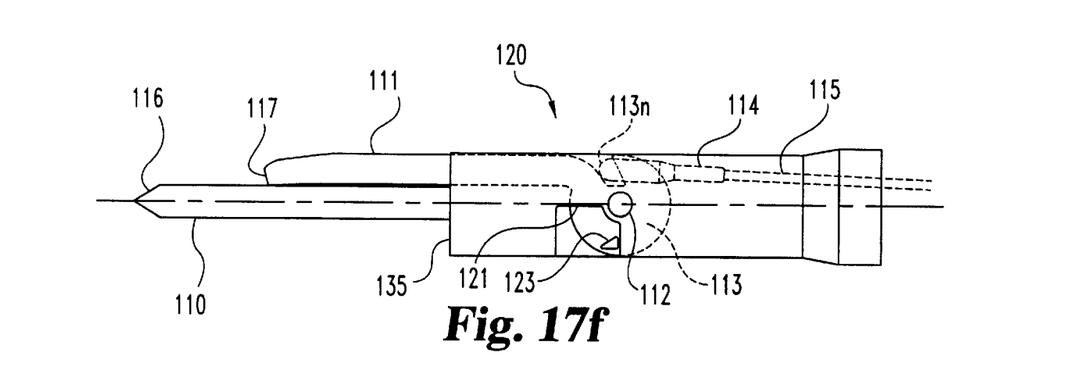
Figure 17G:
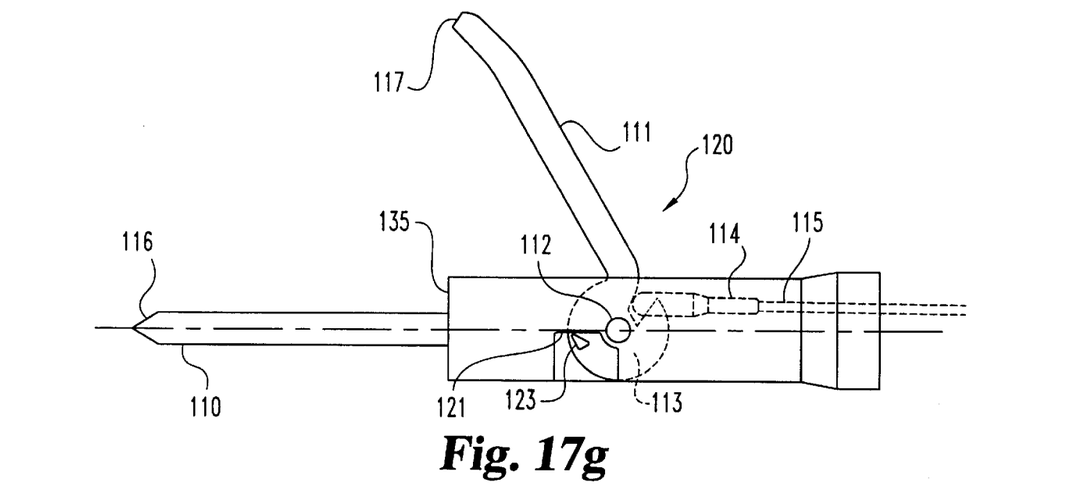

Referring to FIGS. 17e–17g, the cam 113 has notch 113n engaged by lug 114p of a driver 114 which is fixed to the end of drive rod 115. Drive rod 115 may be solid or a hollow tubular structure. The proximal portion of drive rod 115 is threadedly engaged with a threaded insert 153 (see FIG. 17a) fixed within thumb wheel 152 rotatably mounted in the handle 150. Because of the threaded connection, rotation of wheel 152 causes drive rod 115 to retract relative to the outer tubular body 101 and the yoke, thus causing driver 114 to turn cam 113 on its pivot axis, causing guide foot 111 to pivot outward. Handle 150 is affixed to outer tubular body 101 by means of a flush port assembly 130 which has a recess receiving end affixed and sealed to the proximal end of the tubular body 101. The flush port assembly 130 has a tubular post 106 received in a hole in the front portion of the handle and fixed to it by a set screw 151.

The guide foot 111 is kept from pivoting beyond a predetermined maximum radial distance of a circle centered on the spike 110, by a stop wall 121 in a recess in the yoke 120 and a stop lug 123 on the cam 113. The driver 114 has a notch 122 cut therein which is sized to receive the cam portion of the guide foot 111 and angled so that guide foot 111 and cam 113 are engaged and pivoted by movement of driver 114 (see FIGS. 17e–g). The lug 123 on cam 113 engages stop wall 121 of the yoke 120 and prevents cam 113 from pivoting past an angle such that tip 117 of guide foot 111 is more than the predetermined maximum distance from spike 110. The stop wall 121 may be located in various different embodiments so that the tip 117 of guide foot 111 has a predetermined maximum distance of 0.378 inches, 0.416 inches or 0.457 inches. Again the wheel 152 is preferably circular with knurling or other gripping features defined on the circumference of the wheel to facilitate manual rotation of the wheel.

As indicated above, the exterior of outer tubular body 101, handle 150, wheel 152 and flush port assembly 130 are insulated to protect the user from the electrical current. Flush port assembly 130 is used to irrigate the site being marked. Flush port assembly 130 consists of passageway 131 for flushing irrigants through the interior of outer tubular body 101 from the proximal end 103 to the distal end 104 and out through the yoke assembly. Flush port assembly 130 also includes a flush port cap 132 which is removable. When flush port cap 132 is on the flush port assembly 130, it prevents irritants from entering the passageway and gaining access to the site being marked.

At the end of handle 150 most distant from the proximal end 103, is a handle cap 154 with a circular hole in the center through which cautery post 155 or other electrical conducting means passes. Suitable conducting path to the foot 111 is achieved by the materials of the assembly. An insulating coating is provided on the outside of the yoke, tubular body, flush port assembly, handle and, if not otherwise managed, on the thumbwheel too.

Figure 18A:
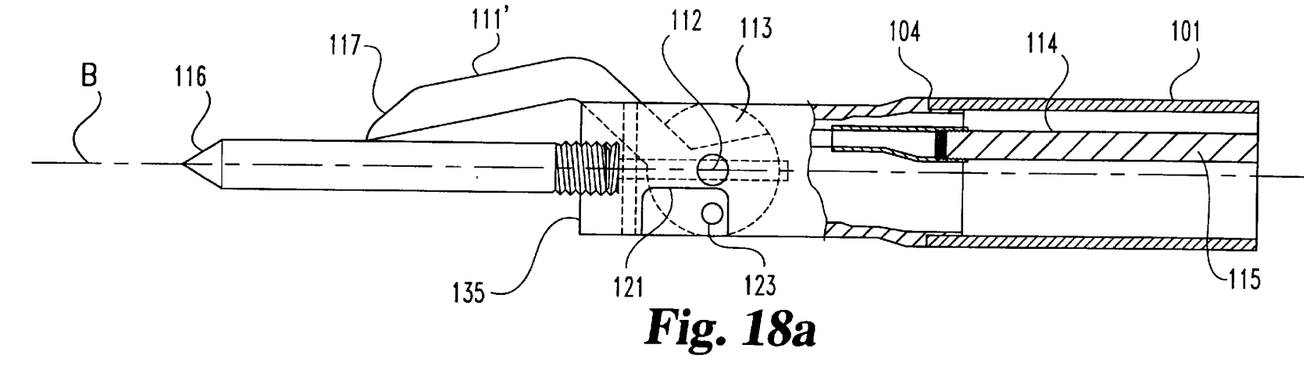
FIG. 18a is an enlarged partial fragmented cross sectional view of another embodiment of the distal tip of the template assembly illustrated in FIGS. 17a–17g, wherein the guide foot has a bend and is in its initial insertion position.
Figure 18B:
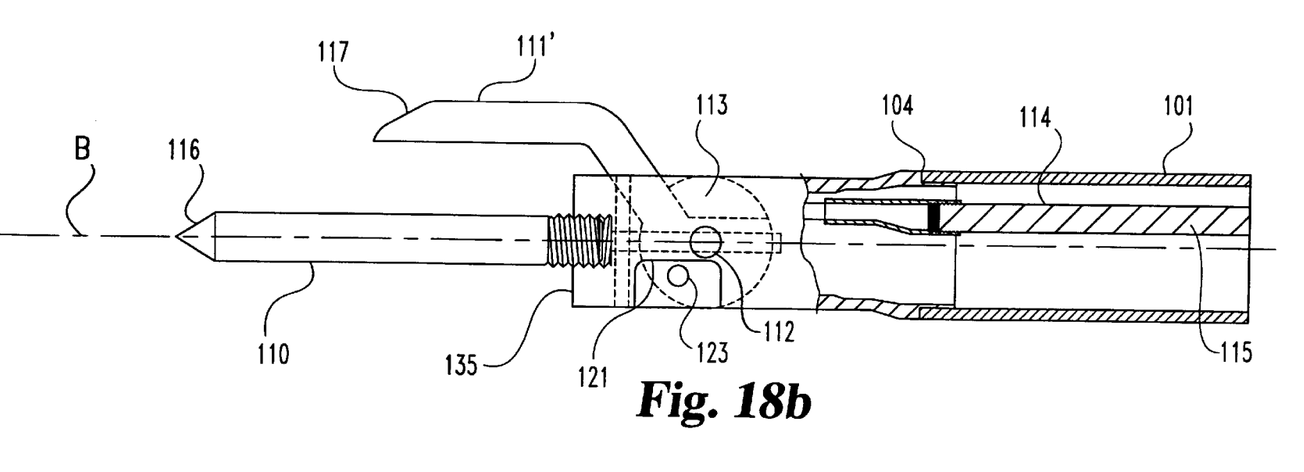
FIG. 18b is an enlarged partial fragmented cross sectional view of the distal tip of the template assembly illustrated in FIG. 18b, shown with the guide foot in its second deployed position.

In one embodiment, as in FIGS. 17a–g, the guide foot 111 is straight. In this embodiment when the patient's skin is penetrated by the distal end of template assembly tip 117 of guide foot 111 is adjacent to spike 110, and, because the foot is straight, guide foot 111 is generally parallel to spike 110. In another embodiment, shown in FIGS. 18a and 18b, the tubular body, flush port assembly 130 and handle 150 can be the same as in FIGS. 17a–17g, but guide foot 111' has a bend in it. This bend is configured so that when guide foot 111' is pivoted away from spike 110, there will be one particular distance separating spike 110 from tip 117 of guide foot 111' where an axis defined by the bend and tip 117 will be generally parallel to spike 110. This is demonstrated in FIG. 18b where cam 113 has been rotated to pivot guide foot 111' to the point where the axis defined by the bend and tip 117 is generally parallel to the longitudinal axis B along which spike 110 extends.

Steps in the use of the template assembly 100 are similar to those depicted in FIGS. 11a–13b. The patient's skin is punctured to receive a sealed trocar 50. With the sealed trocar 50 anchored to the skin S, the template assembly 100 is introduced with the guide foot 111 in its first position, where tip 117 of guide foot 111 is adjacent to spike 110. Spike 110 is advanced toward the disc until the tip 116 of the spike 110 is against the disc annulus D. The location of the spike 110 precisely centered with respect to the desired fusion implant sites in the disc is determined, then the disc is pierced with the spike 110 to anchor the assembly to the disc. The template assembly 100 may then be withdrawn slightly or left in place and guide foot 111 is pivoted to its second position. The drive rod 115 is retracted through the tubular body 101 by rotating the wheel 152. As the wheel 152 is rotated, drive rod 115 retracts causing driver 114 to turn cam 113 to which guide foot 111 is attached. The tip 117 of guide foot 111 pivots away from the longitudinal axis B and spike 110 as in FIG. 17d and FIG. 18b. It is understood that alternative embodiments in which drive rod 115 and driver 114 are advanced, instead of retracted, are within the scope of the invention.

In an alternative embodiment, the wheel 152 is provided with markings to indicate the tip 117 location on a radius of a circle centered on the longitudinal axis B. Thus, the distance the tip 117 moves is known and can be continuously varied from a distance of zero when adjacent to spike 111 to the full extension as constrained by the predetermined maximum distance allowed for by yoke 120 and stop wall 121. In another alternative embodiment when the desired distance has been reached by rotation of wheel 152, the wheel may be locked into position by, for instance, a second set screw. In another embodiment, the wheel 152 is rotated until the guide foot 111 is constrained from pivoting any further by lug 123 and stop wall 121. The predetermined maximum distance allowed for by various stops 121 is set at a distance corresponding to typical implant sizes.

Figure 19:
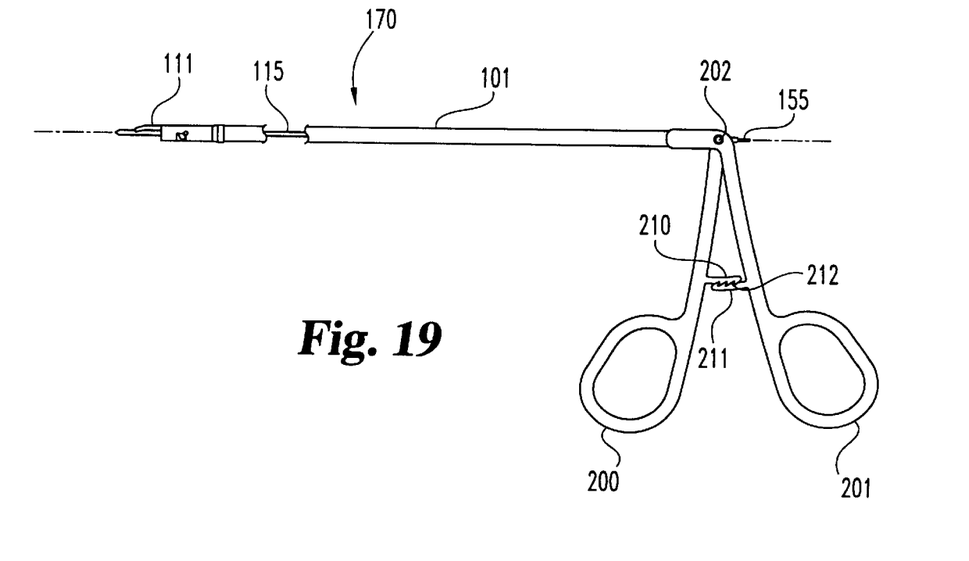
FIG. 19 is a fragmented elevational view of another embodiment of the template assembly wherein the tip portion of the guide foot is shown sectioned.
Figure 20:
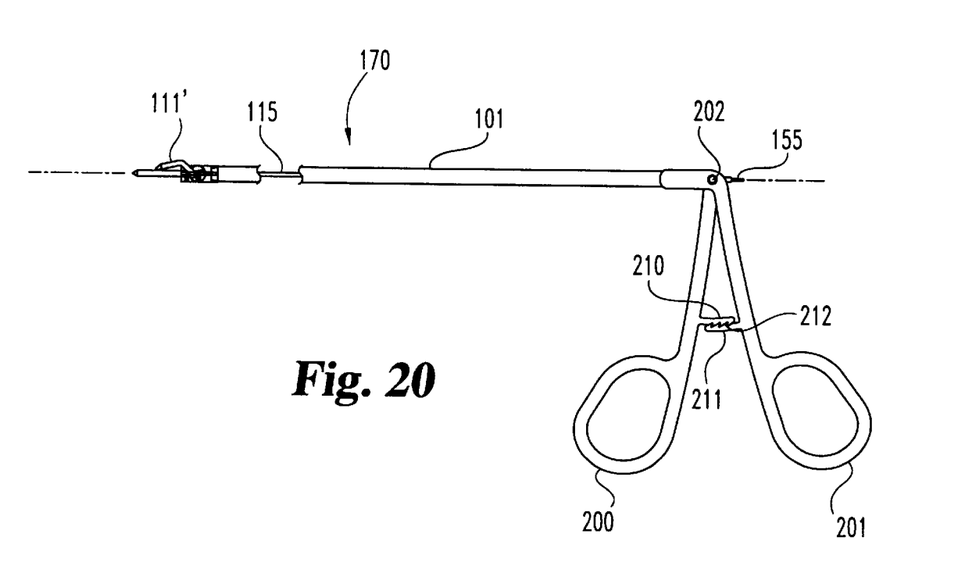
FIG. 20 is a fragmented elevational view of another embodiment of the template assembly of FIG. 19 wherein the tip portion is shown sectioned and the guide foot has a bend in it.

Referring to FIGS. 19 and 20, two other embodiments of template assembly are shown. Like elements are labeled as previously in FIGS. 17a–g and 18a–b. In these embodiments, the deployment means are altered in that instead of wheel 152, handles 200 and 201 are used to control the amount drive rod 115 moves forward. Handle 201 is fixed to tubular body 101 as is the flush port assembly in FIGS. 17a–e. Handle 200 is pivotably connected to handle 201 at pivot pin 202 and is pinned to the proximal end of drive rod 115. In one embodiment, handles 200 and 201 may be closed along a full continuum of distances in which the tip 117 moves.

In an alternative embodiment, a bar 210 extends from handle 200 and a corresponding bar 211 extends from handle 201. Bars 210 and 211 have interlocking jaws or ratchets 212. These ratchets are configured so that a predetermined amount of pivoting occurs resulting in the known distances between tip 117 of guide foot 111 and the central longitudinal axis B. In one embodiment, the bars 210 and 211 have three stops or ratchets. In this embodiment, the stops are preferably configured so that the tip 117 pivots outward a distance of 0.378 inches at the first ratchet, 0.416 inches at the second ratchet, and 0.457 inches at the third ratchet. The central difference between the embodiments in FIGS. 19 and 20 is that in FIG. 19 guide foot 111 is sraight and in FIG. 20 guide foot 111' has a bend in it.

Other than the drive rod 115 being advanced by the handles 200 and 201, the remainder of the template is labeled and functions like the embodiments described in FIGS. 17a–g and 18a–b. For example, if desired, a yoke 120, stop 121 and lug 123 could also be used with the handle deployment means in combination with the ratchets or the continuous mode of operation of the handles described. Alternatively, the handles could be configured with just one stop or ratchet corresponding to a desired distance. In this case, a different instrument would have to be used for each size or distance required between tip 117 and spike 110. It is contemplated as within the scope of the invention that a flush port assembly 130 may be used in this embodiment, along with all other embodiments previously described.

In all of the embodiments in FIGS. 17–20 the guide foot is formed of an electrically conductive material and the tip is configured to emulate the working tip of an electrocautery instrument. The guide foot, cam, driver, and drive rod may all be formed of conductive material so that when an electrical source is attached to cautery post 155, electrical energy flows through to the guide foot. Alternatively, an electrical attachment passing through tubular body (see for example 31' in FIG. 15) may provide electrical energy to guide foot 111, 111'.

While the invention has been described for use in positioning bilateral fusion devices, the same marking capability can be used for other procedures. For example, the template can be used to mark the location for insertion of various instruments and tools into the disc space. Other uses for the template assembly of the present invention may readily present themselves to persons of ordinary skill in this art.

What is claimed is:

1. A template assembly to facilitate the placement of an implant or instrument at a portion of the spine, such as the disc space between adjacent vertebrae, comprising:

a tubular body sized for introduction into a patient for advancement to the portion of the spine, said tubular body having a longitudinal axis, and a proximal end disposed outside the patient and a distal end disposed adjacent the portion of the spine when said body is within the patient;

a spike extending from said distal end of said tubular body along said longitudinal axis of said tubular body, said spike has a tip and is configured for piercing into a disc annulus of said spine, said distal end of said tubular body sized larger than said spike thereby forming a stop to limit the advancement of said template assembly into said disc annulus;

an elongated guide foot with a first end and second end, said guide foot having a rotatable cam adjacent said tubular body at said first end, whereby said guide foot is pivotable between a first position in which said second end is adjacent said spike for introduction into the patient, and a variable second position in which said second end is at a known distance from said spike; and deployment means extending through said tubular body and operating on said guide foot for causing said guide foot to pivot between said first position and said variable second position.

2. The template assembly according to claim 1, wherein said deployment means is connected to a pair of handles, said handles for controlling the pivoting of said guide foot from said first position to said variable second position.

3. The template assembly according to claim 2, wherein said handles are connected by a pair of ratcheted bars.

4. The template assembly according to claim 3, wherein said bars have three ratchet positions, and wherein said three ratchet positions correspond to said known distances of 0.378 inches, 0.416 inches, and 0.457 inches, respectively.

5. The template assembly according to claim 1, wherein said guide foot has a bend in between said first end and said second end, so that an axis defined by a line connecting said bend and said second end is generally parallel to said longitudinal axis of said spike when said guide foot is at a particular second position.

6. The template assembly according to claim 5, wherein said bend is such that said particular second position corresponds to the known distance of 0.378 inches.

7. The template assembly according to claim 1, wherein said guide foot has an axis which is generally parallel to said longitudinal axis of said tubular body when said guide foot is in the first position, and said axis is oriented at an angle relative to said longitudinal axis of said tubular body when said guide foot is in said variable second position.

8. The template assembly according to claim 1, wherein said second end has a tapered tip.

9. The template assembly according to claim 1, wherein said guide foot has an inward bend in between said first end and said second end, such that said second end points towards said spike and said tubular body when said guide foot at said first position.

10. A template assembly to facilitate the placement of an implant or instrument at a portion of the spine, such as the disc space between adjacent vertebrae, comprising:

a tubular body sized for introduction into a patient for advancement to the portion of the spine, said tubular body having a longitudinal axis, and a proximal end disposed outside the patient and a distal end disposed adjacent the portion of the spine when said body is within the patient;

a spike extending from said distal end of said tubular body along said longitudinal axis of said tubular body;

an elongated guide foot with a first end and second end, said guide foot having a rotatable cam adjacent said tubular body at said first end, whereby said guide foot is pivotable between a first position in which said second end is adjacent said spike for introduction into the patient, and a variable second position in which said second end is at a known distance from said spike;

deployment means extending through said tubular body and operating on said guide foot for causing said guide foot to pivot between said first position and said variable second position; and wherein said guide foot includes marking means associated therewith for creating a mark on a spinal disc annulus identifying a location on the annulus, said marking means including;

a tip defined on said second end; and means for providing electrical energy to said tip to heat said tip for cauterizing the disc annulus.

11. The template assembly according to claim 10, wherein said means for providing electrical energy includes:

said guide foot and said tip being formed of an electrically conductive material; and an electrical attachment connected to said guide foot and extending along the length of said tubular body for engagement to a source of electrical energy outside the patient.

12. A template assembly to facilitate the placement of an implant or instrument at a portion of the spine, such as the disc space between adjacent vertebrae, comprising:

a tubular body sized for introduction into a patient for advancement to the portion of the spine, said tubular body having a longitudinal axis, and a proximal end disposed outside the patient and a distal end disposed adjacent the portion of the spine when said body is within the patient;

a spike extending from said distal end of said tubular body along said longitudinal axis of said tubular body;

an elongated guide foot with a first end and second end, said guide foot having a rotatable cam in said tubular body at said first end, whereby said guide foot is pivotable between a first position in which said second end is adjacent said spike for introduction into the patient, and a variable second position in which said second end is at a known distance from said spike;

deployment means extending through said tubular body and operating on said guide foot for causing said guide foot to pivot between said first position and said variable second position, and wherein said deployment means includes a drive rod and a driver within said tubular body, and said drive rod is threadedly engaged to a wheel disposed outside said tubular body, and whereby said drive rod is advanced through said tubular body by rotation of said wheel; and a yoke, said yoke having a notch sized to receive said guide foot therein, said cam having a protuberance for engaging said yoke, said yoke being configured to prevent said guide foot from pivoting beyond a predetermined maximum of said known distance of said variable second position.

13. The template assembly according to claim 12, wherein said known distance is 0.378 inches.

14. The template assembly according to claim 12, wherein said known distance is 0.416 inches.

15. The template assembly according to claim 12, wherein said known distance is 0.457 inches.

16. The template assembly according to claim 12, wherein said guide foot has a bend in between said first end and said second end such that an axis defined by a line connecting said bend and said second end is generally parallel to said longitudinal axis of said spike when said guide foot is pivoted to the predetermined maximum of said known distance.

17. A template assembly to facilitate the placement of an implant or instrument at a portion of the spine, such as the disc space between adjacent vertebrae, comprising:

a tubular body sized for introduction into a patient for advancement to the portion of the spine, said tubular body having a longitudinal axis, and a proximal end disposed outside the patient and a distal end disposed adjacent the portion of the spine when said body is within the patient;

a spike extending from said distal end of said tubular body along said longitudinal axis of said tubular body, said spike has a tip and is configured for piercing into a disc annulus of said spine, said distal end of said tubular body sized larger than said spike thereby forming a stop to limit the advancement of said spike into said disc annulus;

an elongated guide foot with a first end and second end, said guide foot having a rotatable cam in said tubular body at said first end, whereby said guide foot is pivotable between a first position in which said second end is adjacent said spike for introduction into the patient, and a variable second position in which said second end is at a known distance from said spike; and deployment means extending through said tubular body and operating on said guide foot for causing said guide foot to pivot between said first position and said variable second position, and wherein said deployment means includes a drive rod and a driver within said tubular body, and said drive rod is threadedly engaged to a wheel disposed outside said tubular body, and whereby said drive rod is advanced through said tubular body by rotation of said wheel.

18. The template assembly according to claim 17, wherein said wheel is mounted to a handle, and said handle is affixed to the proximal end of said tubular body.

19. The template assembly according to claim 18, wherein said tubular body and said handle are electrically insulated.

20. A template assembly to facilitate the placement of an implant or instrument at a portion of the spine, such as the disc space between adjacent vertebrae, comprising:

a tubular body sized for introduction into a patient for advancement to the portion of the spine, said tubular body having a longitudinal axis, and a proximal end disposed outside the patient and a distal end disposed adjacent the portion of the spine when said body is within the patient;

a spike extending from said distal end of said tubular body along said longitudinal axis of said tubular body;

an elongated guide foot with a first end and second end, said guide foot having a rotatable cam in said tubular body at said first end, whereby said guide foot is pivotable between a first position in which said second end is adjacent said spike for introduction into the patient, and a variable second position in which said second end is at a known distance from said spike;

deployment means extending through said tubular body and operating on said guide foot for causing said guide foot to pivot between said first position and said variable second position, and wherein said deployment means includes a drive rod and a driver within said tubular body, and said drive rod is threadedly engaged to a wheel disposed outside said tubular body, and whereby said drive rod is advanced through said tubular body by rotation of said wheel; and a passageway within said tubular body connecting at least a portion of said proximal end in fluid communication with at least a portion of said distal end.

21. The template assembly according to claim 20, further including an opening of the passageway at said proximal end, and a removable cap sized to fit the opening, said cap configured to prevent the entry of irritants into the patient when attached.

* * * * *